United States Patent [19]

Sheehan

[11] 4,252,117
[45] Feb. 24, 1981

[54] INJECTION DEVICE

[75] Inventor: Neil J. Sheehan, Berkeley, Calif.

[73] Assignee: Cutter Laboratories, Inc., Berkeley, Calif.

[21] Appl. No.: 82,497

[22] Filed: Oct. 9, 1979

[51] Int. Cl.³ .............................................. A61M 5/00
[52] U.S. Cl. ............................... 128/214 R; 285/260; 285/332; 285/417
[58] Field of Search ....................... 128/214 R, 214 G; 285/260, 232, 417, 423

[56] References Cited

U.S. PATENT DOCUMENTS

| | | | |
|---|---|---|---|
| 3,378,006 | 4/1968 | Burke | 128/214 |
| 3,429,311 | 2/1969 | Wickett | 128/214 G |
| 3,512,806 | 5/1970 | Rommey et al. | 128/214 R |
| 4,135,743 | 1/1979 | Hughes | 285/417 X |

*Primary Examiner*—Stephen C. Pellegrino
*Attorney, Agent, or Firm*—Robert E. Allen

[57] ABSTRACT

An improvement in an injection bulb device in an assembly for administration of parenteral solutions is disclosed. The device is a tubular elastomeric member having an enlarged intermediate section whose bore is larger than the bores in the two end sections. A plurality of flat-surfaced projections or rings extend inwardly from the walls of the bores in the end sections which compressively grip the end of a rigid needle adapter and flexible tubing inserted respectively within these end sections. The end of the tubing flares outwardly into the enlarged bore of the intermediate section and this configuration assists in increasing the strength of mechanical engagement between the tubing and the injection bulb.

3 Claims, 5 Drawing Figures

INJECTION DEVICE

BACKGROUND OF THE INVENTION

1. Field:

This invention relates to an improvement in an injection device as part of an assembly for administration of parenteral solutions and the like.

2. Prior Art:

It is a common occurrence in hospitals that during the administration of a parenteral solution to a patient, it becomes necessary that the patient receive a medicament by rapid infusion. The medicament can be introduced by syringe by injecting into a resealable injection device located adjacent the needle of the administration set. This device is commonly referred to as injection bulb. It is made of resilient, elastomeric material and is friction fitted to a generally rigid, plastic needle adapter at one end and to flexible tubing at the other end. The usual solvent sealing techniques which are preferred cannot be applied since the materials of the parts are too dissimilar chemically to bring about an effective seal. Consequently, the parts are held together only as a result of pressures of stressed end portions of the elastomeric member on the needle adapter and flexible tubing.

In certain instances an administration set is subjected to excessive pressures and as sometimes happens the injection bulb separates from either the needle adapter or the tubing resulting in an interruption of flow of fluid into the patient. U.S. Pat. No. 3,378,006 discloses an approach for increasing the resistance against separation. The approach involves providing a series of spaced, inwardly directed, semicircular ribs on the inner surface of the bore at each end portion of the injection bulb. These ribs provide engagement with the needle adapter and tubing at spaced intervals with small annular chambers being formed between the ribs. To assist in the engagement of the flexible tubing with the injection bulb, the tubing is rigidified by a rigid tubular insert. Although such a device is a considerable improvement over other injection bulbs, it requires the rigid insert in the tubing to give a greater degree of assurance that separation at this location does not occur at reasonable overpressures. This adds to the costs and difficulty of manufacture.

SUMMARY OF THE INVENTION

The present invention concerns itself with an improved injection bulb which results in an improved engagement with the tubing and a needle adapter and decreases the likelihood of disengagement of the injection bulb from either the tubing or adapter when normal overpressures are exerted.

The injection bulb comprises an elastomeric, tubular member with an enlarged intermediate section having a bore which is larger than the bores in the two end sections. The inner walls of the end sections have a plurality of spaced inwardly projecting flat-surfaced rings for compressively engaging the adapter at one end and flexible tubing at the other end. The tubing is additionally secured by virtue of its end being flared and extending slightly into the enlarged bore of the intermediate section.

In addition to the improved tubing and adapter engaging features of the injection bulb, and invention also includes an improvement in target sites located on the enlarged intermediate section of the bulb. It is standard practice to provide target sites on injection bulbs in the form of raised rings or the like to mark suitable locations for inserting the needle of a medicament syringe. Target sites are invariably swabbed with alcohol or the like to cleanse the area prior to needle insertion. Because of the obstructing structure of the target rings, the surface within the ring does not get adequately cleaned and some of the debris or other contaminants which might reside on this surface will not be removed and will be carried into the interior of the bulb by the needle. The target sites of the present invention comprise raised flat-surfaced projections, preferably located on a sloping shoulder of the intermediate section adjacent the end attached to the tubing. Swabbing of these targets sites provides surfaces which are clean and substantially free of contaminating material.

DETAILED DESCRIPTION OF A PREFERRED EMBODIMENT

Figure 1:
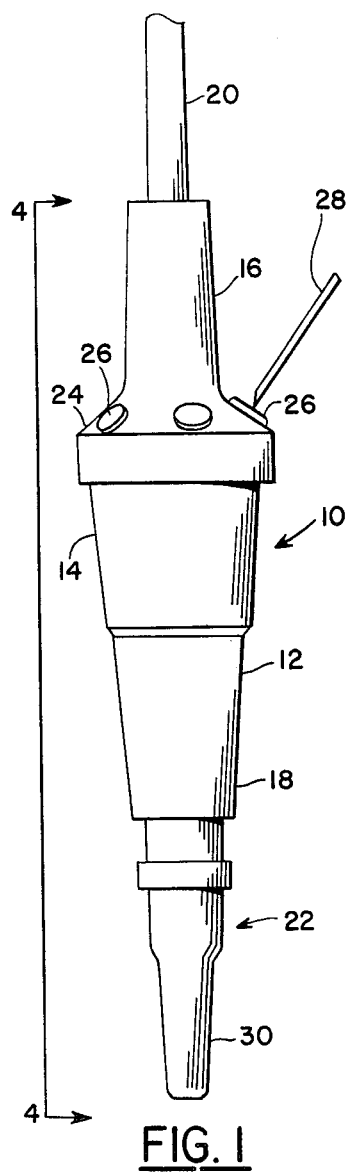
FIG. 1 is a view of a preferred embodiment of an injection bulb of the present invention showing the bulb attached to tubing and a needle adapter.

FIG. 1 illustrates a preferred embodiment of an injection bulb 10 attached to a flexible conduit or tubing 20 and a needle adapter 22. Tubing 20 communicates with a supply of a parenteral solution or the like intended for intravenous administration. Adapter 22 has a tapered outer end 30 adapted for attachment of a needle intended for venipuncture.

Injection bulb 10 comprises a tubular, elastomeric member 12 having an enlarged intermediate section 14 between ends 16 and 18. The bore of intermediate section 14 is considerably larger than the bores within end sections 16 and 18. The area between end section 16 and intermediate section 14 has a sloping shoulder 24 on which a number of flat-surfaced projections or target sites 26 are located. These target sites 26 pinpoint locations better suited for the insertion of a needle 28 of a medicament syringe into the interior or bore of the intermediate section 14. Other types of target sites may also reside on shoulder 24 such as raised annular rings or the like but the specific flat-surfaced projections 25 are preferred since the surface on these projections are more effectively cleansed by swabbing and therefore greatly reduce the chance of possible contamination of a needle as it is inserted through the site.

Projecting inwardly from the surface of the bores in the end sections 16 and 18 of injection bulb 10 are a number of flat-surfaced rings 32, 34, 36 and 38. In this embodiment of the injection bulb 10, there are two such rings in each end section which are located adjacent the bore of the intermediate section 14. Needle adapter 22 has a luer tapered end 30 adapted for the attachment of a hub of a venipuncture needle, an intermediate hub portion 40, and an end portion 42 which is inserted into the bore of end section 18 of injection bulb 10. Adapter 22 is made of rigid, transparent or translucent material such as polyethylene or polypropylene and the end portion 42 preferably tapers slightly for easier insertion into the end section 18. The outer diameter at the outer end of end portion 42 is slightly larger than the diameter of any portion of the base in end section 18 (excluding the tapered bore at mouth 39) so that after insertion of adapter 22 into end section 18, the elastomeric walls of end section 18 are stretched and exert a compressive force on end portion 42. This force is even greater on the end portion 42 where its surface contacts flat rings 36 and 38 by virtue of the smaller diameters of the bore at these positions.

Tubing 20, which may be made of flexible material such as polyvinyl chloride, has an outside diameter slightly larger than the largest diameter of the bore in end section 16 (excluding the tapered bore at mouth 37). The provision of ring 34 adjacent the enlarged bore of the intermediate section 14 and ring 32 results in an engagement of tubing 20 with end section 16 which is much stronger than other arrangements currently in use such as rigid tubular inserts in the end of the tubing which is compressed within a bore where there are no internal rings. In the assembly of the various parts, tubing 20 is inserted so that its end 44 is made to project at least slightly beyond the bore of section 16 and into the enlarged bore of the intermediate section 14. During conventional heat sterilization of administration sets with this arrangement of tubing 20, the end 44 flares out and this portion, as well as the portions of tubing under compression by rings 32 and 34, take a set upon cooling. This flared portion and the definite angular surfaces of the tubing between and adjacent the rings 32 and 34 all contribute to a mechanical locking of the tubing within the end section 16.

Strength of the attachment of tubing and of the needle adapter to the injection bulb of this invention was compared with attachment strength at these connections with injection bulbs in administration sets of three commercially available sources. The tests were conducted as follows. The outlets of the needle adapters were closed off by capping and the tubing extending from the injection bulbs was connected to a pressure gauge followed by an IVAC 530 intravenous pump which was connected to a container of water. The injection bulbs in each instance were loosely surrounded by a short piece of PVC tubing to prevent ballooning of the enlarged intermediate section. The pump was started after setting for a flow rate of 5 ml. per minute and the pressure was noted at the point where separation or "blow-off" occurred at either connection. Usually, "blow-off" first took place at the connection with the needle adapter. The end section which has been connected to the adapter would then be clamped off and pressure then applied until blow-off occurred at the tubing connection. In the event the tubing separated first, the needle adaptor was then connected to the tubing from the gauge, the opposite end of the injection bulb was clamped off and pressure then applied.

Figure 2:
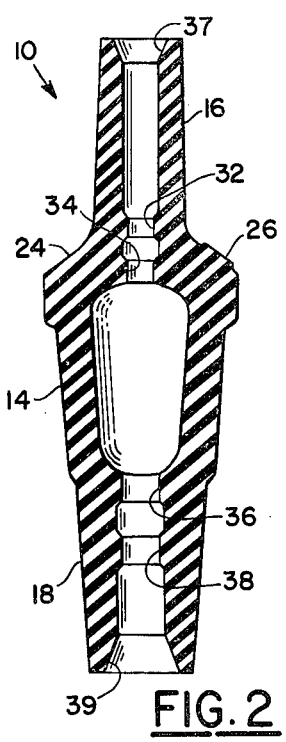
FIG. 2 is a view in cross section of the injection bulb of FIG. 1.
Figure 3:
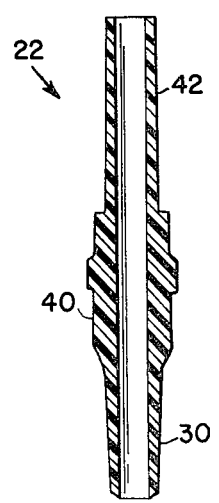
FIG. 3 is a view in cross section of the needle adapter.
Figure 4:
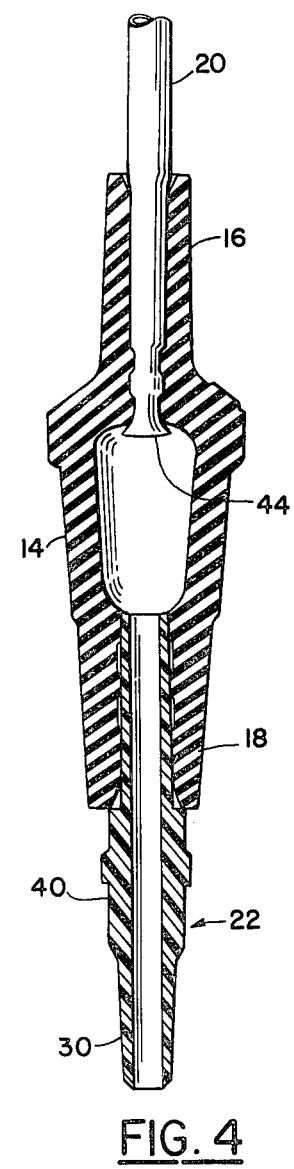
FIG. 4 is a view in cross section of the injection bulb attached to the needle adapter and tubing as shown in FIG. 1 taken along the line 4—4.
Figure 5:
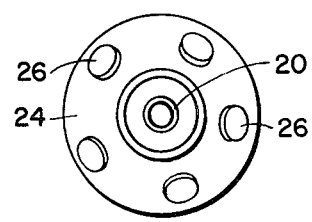
FIG. 5 is a plan view of the injection bulb of FIG. 1.

Twenty-eight samples of commercial product A and 36 samples of commercial product B were tested. The connecting ends of the bulbs on each of these products had uniform bores and the portion of tubing within the bulb had rigid plastic inserts. Three samples of product C were also tested. These were similar to the assembly as shown in FIG. 2 of previously discussed U.S. Pat. No. 3,378,006. Seventy samples of the product of the present invention were tested for comparison.

TABLE 1

Strength of Tubing and Adaptor Connections on Injection Bulbs

| Product | Blow-Off Pressures, lbs./in.$^2$ | |
|---|---|---|
| | At Adaptor Connection | At Tubing Connection |
| A | 29.9$^a$ | 30.8 (rigid inserts) |
| B | 28.9 | 34.6 (rigid inserts) |
| C | 32.0 | 36.7 (rigid inserts) |
| Invention | 36.3 | 36.7 (no inserts) |

$^a$These are averages on the number of samples tested.

It becomes apparent that the improved design of the engagement means for tubing and needle adapter in the present invention provides considerably superior protection against separation when pressures are applied. The presence of rigidifying inserts in the tubing alone are not sufficient (Products A and B). Product C requires both the insert and internal rings in the bore to achieve the same high protection against "blow-off" as that for the product of the invention whose flat-surfaced interior rings only (no insert) are sufficient. On the adapter connection, internal rings in the bore are essential and give superior protection against separation only if the rings are flat-surfaced (Product of the Invention) rather than being semicircular (Product C).

Variations within the spirit of this invention are possible and therefore it is intended that the specific example described above should be construed as illustrative only and the scope of the invention should be limited only by the claims which follow.

I claim:

1. In an assembly for administering parenteral fluids, including a rigid needle adapter connected to an injection bulb which is joined to a flexible conduit adapted for communication with a supply of parenteral fluid, the improvement wherein the injection bulb comprises an elastomeric tubular member with an enlarged intermediate portion between a first end portion and a second end portion, a bore in the intermediate portion which is larger than a bore in either end portions, the surface of the bores in the first and second end sections having a plurality of spaced, inwardly projecting, rings substantially flat on their innermost surfaces adapted to compressively engage a portion of the outer surfaces of the adapter and the conduit respectively, the conduit extending all the way through the bore of the second end portion with its end extending into and flaring outwardly into the larger bore of the intermediate portion.

2. The assembly of claim 1 wherein there are two rings extending inwardly in the bores of the first and second end portions, the two rings being closely spaced and located adjacent the bore of the intermediate portion.

3. The assembly of claim 1 or 2 wherein the intermediate portion has a sloping outer shoulder at the point where the intermediate portion joins the second end portion, the sloping shoulder further including a plurality of outwardly projecting target sites having flat outer surfaces.

* * * * *